United States Patent
Virág et al.

(10) Patent No.: US 7,327,515 B2
(45) Date of Patent: Feb. 5, 2008

(54) SLIDE FEEDING UNIT FOR AN AUTOMATIC SCANNING MICROSCOPE

(75) Inventors: Tibor Virág, Budapest (HU); Attila László, Budapest (HU); Viktor Sebestyén Varga, Pécel (HU); Béla Molnár, Budapest (HU)

(73) Assignee: 3dhistech KFT, Budapest (HU)

( * ) Notice: Subject to any disclaimer, the term of this patent is extended or adjusted under 35 U.S.C. 154(b) by 0 days.

(21) Appl. No.: 10/562,500

(22) PCT Filed: Feb. 27, 2004

(86) PCT No.: PCT/HU2004/000019

§ 371 (c)(1),
(2), (4) Date: Sep. 25, 2006

(87) PCT Pub. No.: WO2004/113989

PCT Pub. Date: Dec. 29, 2004

(65) Prior Publication Data

US 2007/0103772 A1    May 10, 2007

(30) Foreign Application Priority Data

Jun. 24, 2003    (HU) .................................... 0301911

(51) Int. Cl.
*G02B 21/26* (2006.01)
(52) U.S. Cl. ........................ 359/391; 359/394; 359/896
(58) Field of Classification Search ........ 359/368–398, 359/896
See application file for complete search history.

(56) References Cited

U.S. PATENT DOCUMENTS

| 4,248,498 | A | | 2/1981 | Georges ..................... 359/393 |
| 4,427,332 | A | * | 1/1984 | Manriquez ............. 414/331.18 |
| 4,761,075 | A | | 8/1988 | Matsushita et al. ........... 356/39 |
| 4,801,431 | A | | 1/1989 | Cuomo et al. .............. 422/104 |
| 5,000,554 | A | * | 3/1991 | Gibbs ......................... 359/393 |
| 5,646,776 | A | * | 7/1997 | Bacchi et al. ............... 359/393 |
| 5,690,892 | A | | 11/1997 | Domanik et al. ............. 422/63 |
| 5,853,666 | A | | 12/1998 | Seaton et al. ................. 422/65 |
| 6,847,481 | B1 | * | 1/2005 | Ludl et al. .................. 359/391 |

* cited by examiner

*Primary Examiner*—Thong Q Nguyen
(74) *Attorney, Agent, or Firm*—Young & Thompson

(57) ABSTRACT

A slide feeding unit for a microscope includes a slide magazine having a base plate; a toothed rack secured to a magazine side wall; and slide guiding elements perpendicular to an open magazine side. The unit further includes a magazine moving mechanism having a magazine-receiving trough including opposite side plates. Two rotary shafts supported by the trough extend along the trough side plates. Magazine-advancing feeding gears are supported by the side plates and may mesh with the toothed magazine rack. Lifting gears, held in the side plates, have pins on which the magazine is supported when raised or lowered. Driving worm gears are rotated by the shafts and mesh with the lifting gears. The unit also includes a slide feeding device having a robot arm displaceable perpendicularly to the direction of advance of the magazine for removing a slide from the magazine.

10 Claims, 4 Drawing Sheets

SLIDE FEEDING UNIT FOR AN AUTOMATIC SCANNING MICROSCOPE

BACKGROUND OF THE INVENTION

This invention relates to a slide feeding unit for an automatic scanning microscope, wherein the feeding unit includes a slide magazine, a magazine moving mechanism and a slide feeding device.

In the field of pathological research and also, in every-day medical practice there is an ever-increasing need for the application of complex data processing, record keeping and archiving systems, as well as for the interactive consulting possibilities of examination results.

While most developments have been directed to the integration of existing microscopes into systems of the above-outlined type, such an integration is feasible only to a limited extent in microscopes well proven for manual examinations, given the particularities of microscopes of such a design. For example, to take advantage of the speed inherent in digital data processing, a slide feeding system is definitely required which is capable of serving high-performance, automatic slide-digitizing microscopes. For these reasons solutions have been developed which provide for an automatic feed (dosing) of microscope slides.

International Patent Application WO9739348 proposes a solution concerning the problem of transporting microscope slides in a vertical direction. The transporting mechanism includes a pair of vertically side-by-side disposed belts. Each belt is provided with plates oriented in a comb-like pattern perpendicularly to the belt surface. The belts are driven in opposite directions of rotation, so that the plates facing one another between the two belts always move co-directionally (upward or downward). Thus, during transport, the slide, supported by two aligned plates forming a plate pair, is either raised or lowered in a substantially horizontal orientation. At the location where the plates of the plate pair diverge, the slide glides out of the plate pair and may be deposited, for example, on another slide or may drop into a storage box.

The above-described solution, however, does not ensure the correct positioning of the specimens and further, because of the vertical transport direction, such a solution cannot be used in case of a given, optical microscope arrangement.

International Patent Application WO0214877 relates to an apparatus for storing, transporting, arranging and preparing microscope slides. The described slide array preparing device (which may be, for example, a device for applying biological specimens to the slides) includes an elevator unit which raises the slides—taken from an associated storage unit—to the level of the work table forming part of the device. At that position the slides are brought into the desired orientation by an adjusting mechanism. Thereafter a depositing unit, displaceable on a stand and including a vacuum chuck for immobilizing the slides, individually removes the slides and organizes them in array form.

The above-outlined apparatus which has been primarily developed for slide-array printing, has the significant advantage that it eliminates error possibilities derived from a manual positioning of the slides, apart from disposing of time-intensive human labor. The apparatus, however, is voluminous as a whole, and its units are complex mechanical arrangements optimized for their tasks to be performed while the slide dwells in the printer. Thus, such an apparatus would not ensure a sufficient working speed in other fields of application.

SUMMARY OF THE INVENTION

It is an object of the invention to provide an improved slide feeding unit which is capable of serving a high-performance automatic scanning microscope, which ensures a substantially faster operation than has been possible in conventional feeding systems of the type described earlier and which is adapted for broader applications, also in case of existing automatic scanning microscopes.

The principle of the invention is based on the recognition that a simple and operationally safe mechanical feeding device may be provided by means of driving worms and gears by mounting a toothed rack on the side of the slide magazine, in meshing relationship which with feeding gears. Further, one part of the feeding gears is configured as a lifting gears having pins that raise or lower the magazine. Also, for manipulating the slides a slide feeding device is provided which includes a robot arm.

Accordingly, the above-stated object and others to become apparent as the specification progresses, are accomplished by the invention, according to which, briefly stated, the slide feeding unit for a microscope includes a slide magazine which has a base plate; two end walls; a side wall; an open side; a toothed rack secured externally to the side wall and being perpendicular to the base plate; and slide guiding elements oriented perpendicularly to the open side. The unit further includes a magazine moving mechanism which has a trough for receiving the magazine in a fitting relationship with the magazine base plate and with the magazine end walls. The trough has opposite side plates each provided with openings. The magazine moving mechanism further has two shafts rotatably supported by the trough and extending along the trough side plates, respectively; a drive for rotating the shafts; feeding gears rotatably supported in respective openings of the side plates and adapted to mesh with the toothed rack for advancing the magazine in a direction of advance; lifting gears rotatably held in the side plates substantially coplanar with an inner surface of the side plates. Each lifting gear has a pin oriented perpendicularly to the lifting gear face. Pins on the lifting gears supported on one of the side plates are in alignment with pins on the lifting gears supported on the other of the side plates. Driving worm gears are rotated by the shafts and mesh with the lifting gears. The unit also includes a slide feeding device traversing the trough and having a robot arm displaceable perpendicularly to the direction of advance of the magazine for removing a slide from the magazine; and a drive for moving the robot arm.

The driving element for the robot arm advantageously includes a motor and a control spindle expediently coupled to the motor by a force-limiting shaft switch (limit switch). In this manner the rotation of the motor may be transmitted to the control spindle, and in case the control spindle is prevented from rotating (for example, the robot arm is jammed or reaches the end of its travel path), the limit switch disconnects the motor from the control spindle, whereupon the motor may freely continue its rotation.

Advantageously, the limit switch includes a sleeve keyed to the motor shaft, a helical spring wound on the exterior of the sleeve and a driven disk cooperating with a bent-out terminus of the helical spring.

According to another advantageous feature of the invention the robot arm includes front and rear slide-moving arms. Further, the robot arm expediently also has a rocking hold-down plate disposed between the two slide-moving arms. In this manner the slides may be moved along the longitudinal axis of the robot arm as they are disposed between the two arms and clamped by the hold-down plate. The raising and lowering of the hold-down plate is advantageously controlled by dogs affixed to the robot arm, so that the hold-down plate can support and then release the advancing slide.

According to yet another advantageous feature of the invention the side walls of the trough of the magazine moving mechanism have vertically-oriented rails which guide the magazines in a vertical direction. By virtue of such an arrangement a plurality of superposed magazines may be disposed between the rails. The magazines then may be automatically fed to the magazine moving mechanism.

DESCRIPTION OF THE PREFERRED EMBODIMENT

Figure 1:
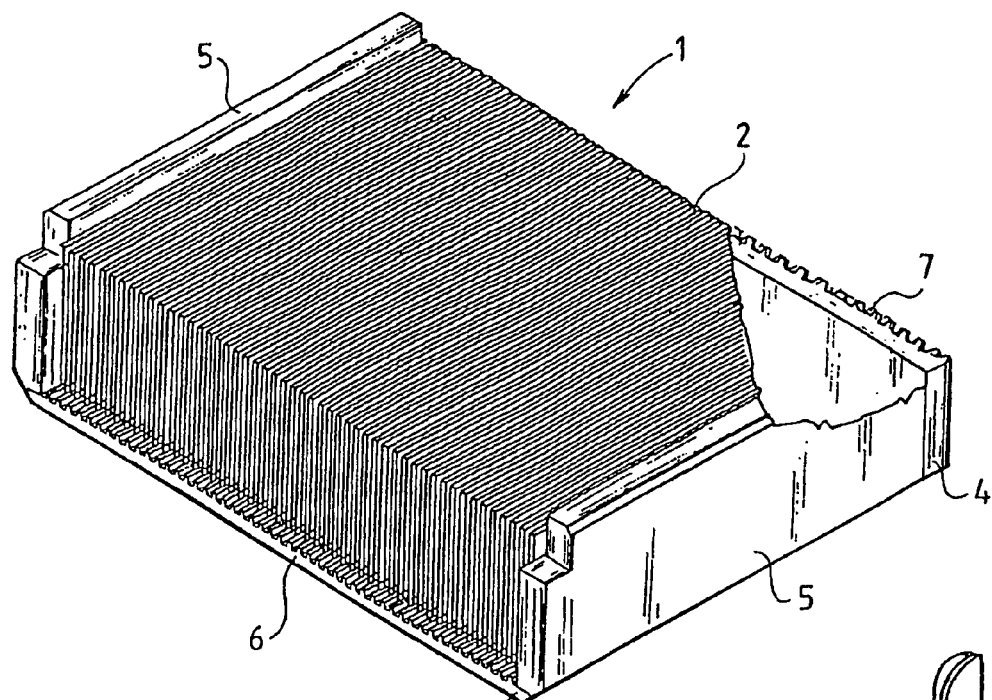
FIG. 1 is a perspective, partially broken-away view of a slide magazine according to the invention.

FIG. 1 shows a microscope slide magazine 1 structured according to the invention, receiving microscope slides 2. The magazine 1 has a base plate 3, a side wall 4 and two end walls 5. The upper face 6 of the base plate 3 is provided with rails between which the slides 2 may be inserted through the open side of the magazine 1. The side wall 4 is provided with a toothed rack 7.

Figure 2:
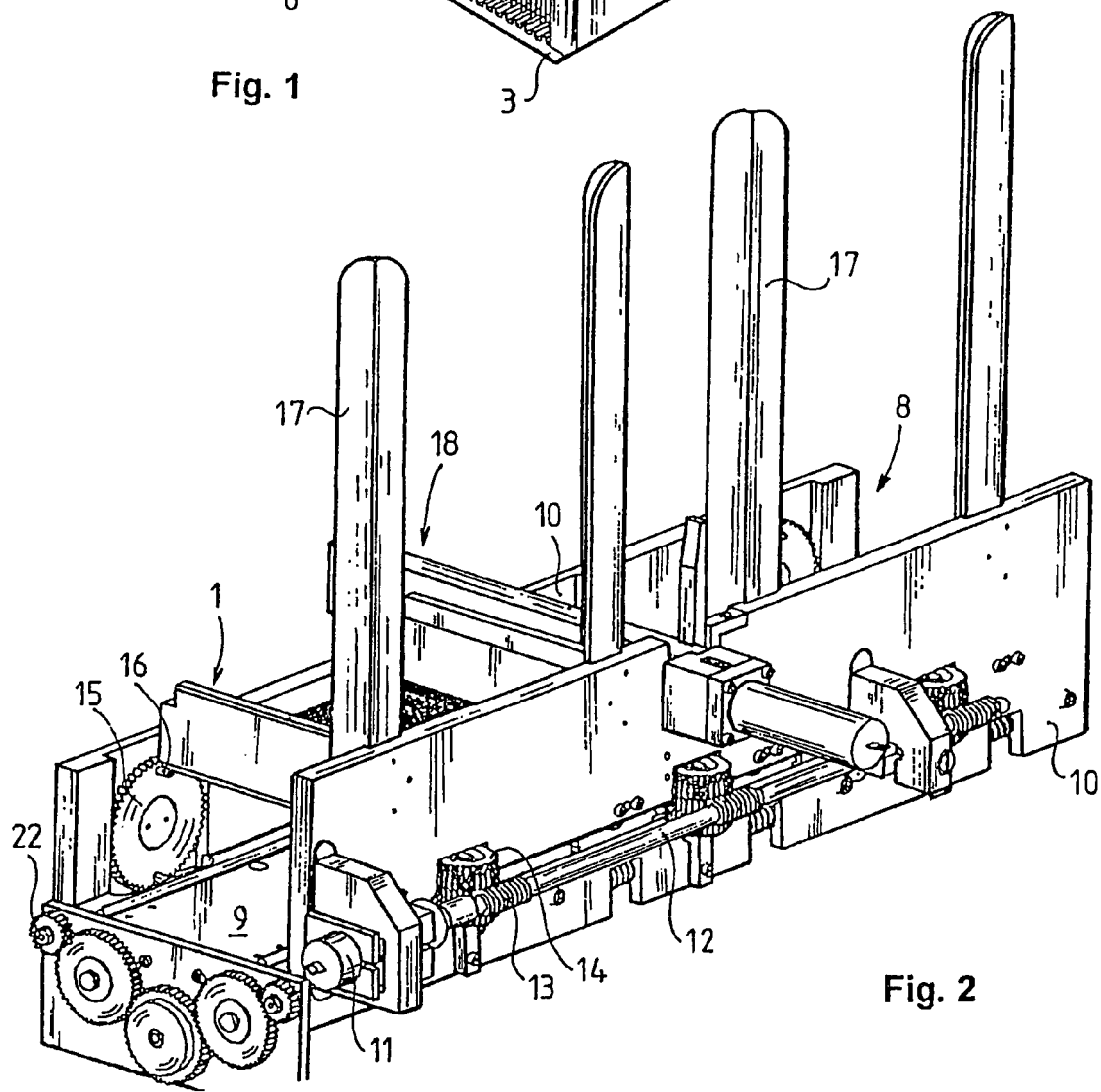
FIG. 2 is a perspective view of a magazine moving mechanism according to the invention.

FIG. 2 shows the magazine moving device which includes a trough 8 formed of a bottom plate 9 and opposite side plates 10. The trough 8 is dimensioned in such a manner that the magazine 1, inserted into the trough 8 with the magazine walls 5 perpendicular to the trough plates 10, fits into the inner construction of the trough 8. A shaft 12 driven by a servomotor 11 is disposed externally of one of the side plates 10 and extends therealong, parallel thereto. The shaft 12 includes two in-phase driving worm gears 13 which mesh with respective feeding gears 14 rotatably supported in openings provided in the side plate 10. On each side plate 10 two pairs of lifting gears 15 are mounted; their axis of rotation is oriented perpendicularly to the side plates 10. Each lifting gear 15 is, on its surface oriented toward the inside of the trough 8, provided with two pins 16 extending perpendicularly from the lifting gear surface and situated at opposite ends of the lifting gear diameter. To the side plates 10 rails 17 are affixed which vertically guide the magazines 1. A slide feeding device 18 traverses the side plates 10 in the space between two pairs of rails 17. The slide feeding device 18 is oriented perpendicularly to the side plates 10.

Figure 3:
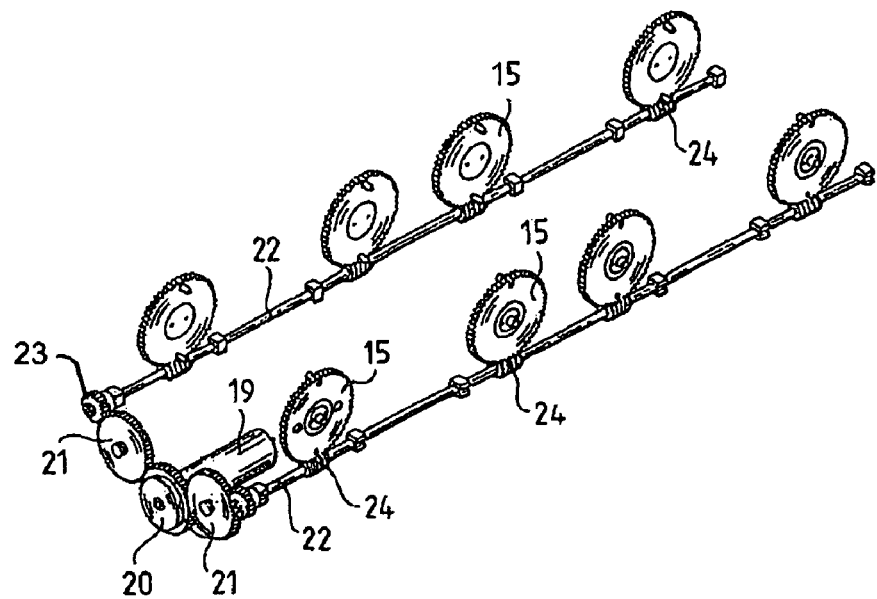
FIG. 3 is a perspective view of a gearing forming part of the mechanism shown in FIG. 2 for vertically displacing the slide magazine.

FIG. 3 separately shows the driving system for the lifting gears 15 according to the embodiment of FIG. 2. At one end of the trough 8, underneath the bottom plate 9 a servomotor 19 is disposed, whose shaft carries a spur gear 20 meshing with two transmission gears 21 circumferentially spaced from one another along the spur gear 20. The transmission gears 21, in turn, mesh with respective pinions 23 attached to an end of respective shafts 22. To each shaft 22 driving worm gears 24 are affixed. Two adjoining worm gears 24 on each shaft form a worm gear pair of opposite pitch. Respective lifting gears 15 noted earlier in conjunction with FIG. 2 mesh with the driving worm gears 24.

It is advantageous if the magazine moving mechanism is arranged in a tilted position wherein the magazines are tilted backward, their base plates including an angle of about 10 to 45° with respect to a horizontal plane. In this case, there is no need of matching the slides, they will automatically take up the right position upon inserting them into the magazines. This will result in a simple handling on the one hand and operational safety on the other hand.

Furthermore, there is no need of dead spots as in revolving magazines. There is a need for a volume of about 18 slides in a revolving magazine receiving 6 slides.

In the description which follows the operation of the magazine moving mechanism will be set forth.

Figure 4:
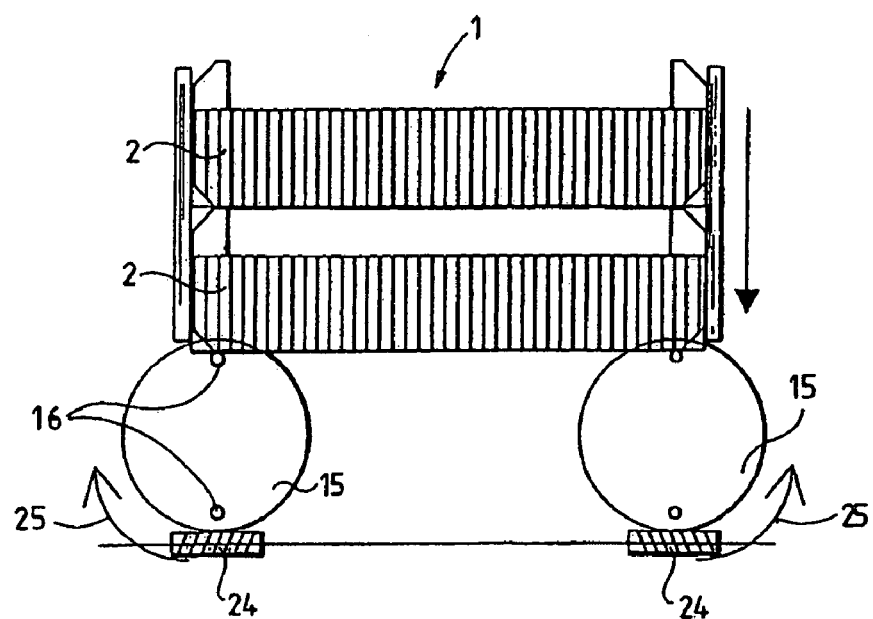
FIG. 4 is a schematic side elevational view illustrating the lowering of the slide magazine into the magazine moving mechanism.

Reverting to FIG. 2, the magazines 1 are placed between the guide rails 17 situated at one end of the trough 8 and are thereafter lowered to the bottom of the trough 8 by means of the descending pins 16 upon rotation of the lifting gears 15, as illustrated in FIG. 4. Thus, as the lowering of the magazines 1 begins, the diameters of the lifting gears 15 determined by the pins 16 are parallel with the guide rails 17; the lowermost magazine 1 is supported by the upper pins 16 of the lifting gears 15. Subsequently, the driving worm gears 24 of opposite pitch rotate the lifting gears 15 in opposite direction as indicated by the arrows 25. During one half revolution of the lifting gears 15 the lowermost magazine 1 supported on the pins 16 sinks at the bottom of the trough 8.

Thereafter, the lowermost magazine 1 is advanced by the magazine moving device to the slide feeding mechanism 18 and then to the rails 17 situated at the opposite end of the trough 8 where, by reversing the operation of the earlier described lowering mechanism, the magazine 1 may be lifted out of the trough 8. The longitudinal displacement of the magazine 1 is effected by the feeding gears 14 supported in the side plates 10 of the trough 8 and the toothed racks 7 disposed on the side wall 4 of the magazines 1. The driving worm gears 13 formed on the shaft 12 rotated by the servomotor 11 drive the feeding gears 14 which advance the magazines 1 by virtue of meshing with the toothed racks 7.

The slide feeding mechanism 18 will now be described in detail with reference to FIGS. 5-10.

Figure 5:
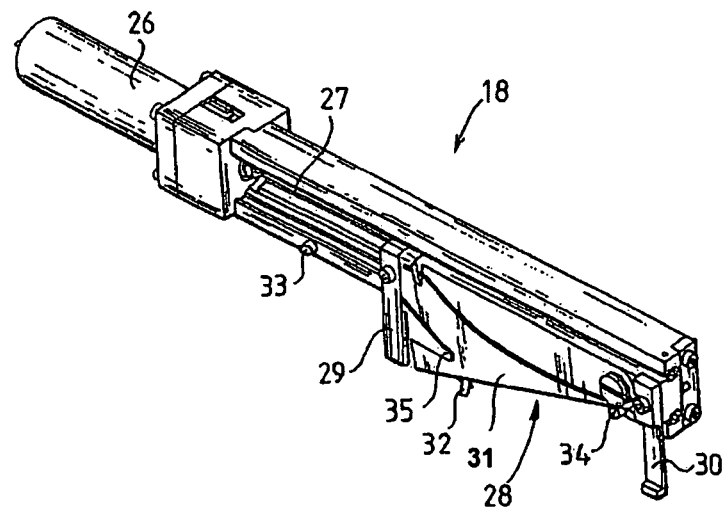
FIG. 5 is a perspective view of the slide feeding device according to the invention.

Turning to FIG. 5, the slide feeding mechanism 18 illustrated therein includes a reversible motor 26, a driving element formed by a control spindle 27 and a robot arm 28. The robot arm 28 has rear and front arms 29 and 30, respectively, which are spaced from one another at a distance that corresponds to the width of the slides 2. Between the arms 29 and 30 a hold-down plate 31 is situated which is mounted on the robot arm 28 such that it may execute rocking motions about a horizontal axis oriented perpendicularly to the robot arm 28. A fork 32 is arranged at the lower edge of the hold-down plate 31 for supporting the slide in motion. The robot arm 28 carries two dogs 33 and 34 spaced from one another longitudinally along the robot arm 28. The dog 34 is located adjacent the free end of the robot arm 28, while the dog 33 is disposed remotely therefrom. At that side of the hold-down plate 31 which is opposite its attachment to the robot arm 28 (that side is oriented toward the front arm 30), a control track 35 is arranged for receiving the dog 33.

Figure 6:
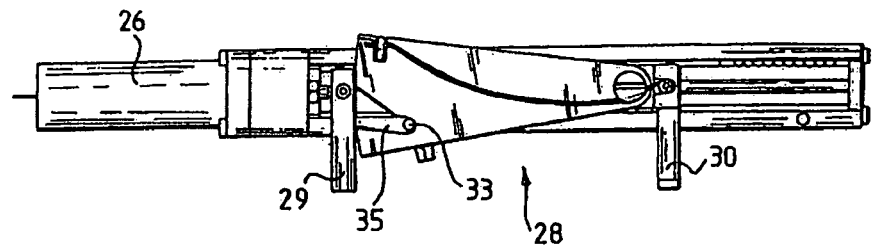
FIG. 6 is a side elevational view of the slide feeding device shown in FIG. 5, illustrated with a fully retracted robot arm.
Figure 7:
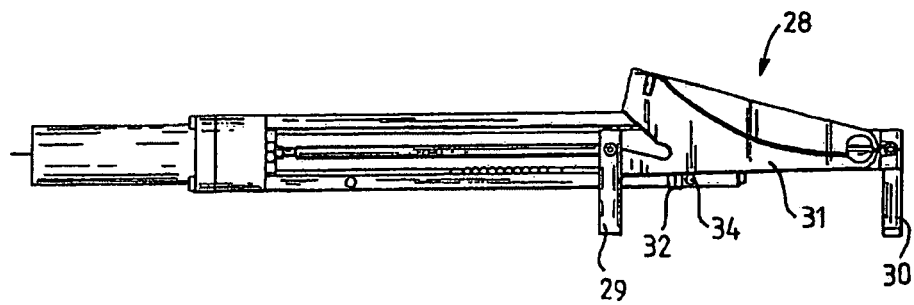
FIG. 7 is a side elevational view of the slide feeding device shown in FIG. 5, illustrated with a fully extended robot arm.

FIGS. 6 and 7 depict the slide feeding mechanism 18 with the robot arm 28 fully retracted and fully extended, respectively. In the fully retracted position of the robot arm 28 the dog 33 is introduced into the control track 35 of the hold-down plate 31, while in the fully extended state of the robot arm 28 the lower edge of the hold-down plate 31 is supported on the dog 34, and the fork 32 is situated between the supporting point and the rear arm 29.

Figure 8:
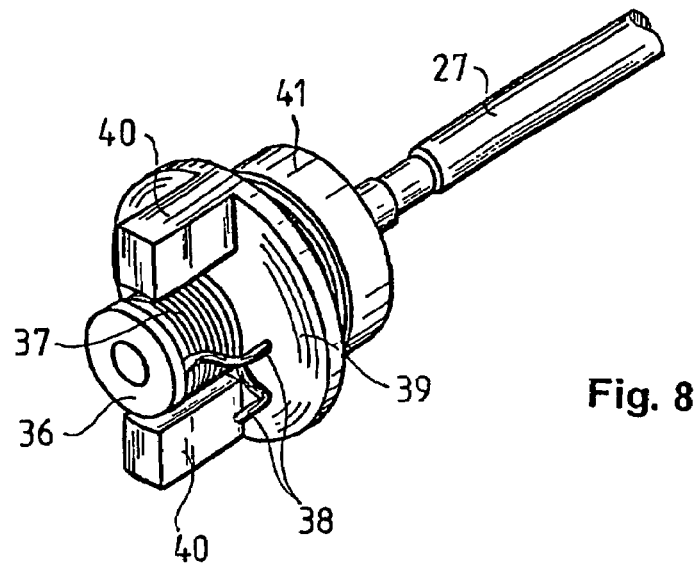
FIG. 8 is a perspective view of a limit switch forming part of the slide feeding device.

The reversible motor 26 is coupled to the control spindle 27 by a limit switch which is shown in detail in FIG. 8. The limit switch includes a sleeve 36 affixed to the shaft of the motor 26, a helical spring 37 wound in a pre-tensioned manner on the exterior of the sleeve 36 and a driven disk 39 cooperating with the bent-out ends 38 of the helical spring 37. The driven disk 39 is provided with two abutments 40 and is coupled to a bearing 41 of the control spindle 27. The bearing 41 is preferably a deep-grooved ball bearing to ensure a true central rotary motion.

In the description which follows the operation of the limit switch will be set forth.

As the sleeve 36 is rotated by the motor 26, one of the ends 38 of the helical spring 37 is pressed against that abutment 40 of the driven disk 39 which is situated in the direction of rotation. As a result, the disk 39 starts rotating, and the rotation is transmitted to the control spindle 27. In case the advance of the slide 2 moved by the robot arm 28 is impeded, the disk 39 stops and thus immobilizes the bent-out end of the helical spring 37, whereupon the latter loses its bias and thus is disengaged from the sleeve 36, so that the motor 26 may freely continue its rotation.

Figure 9:
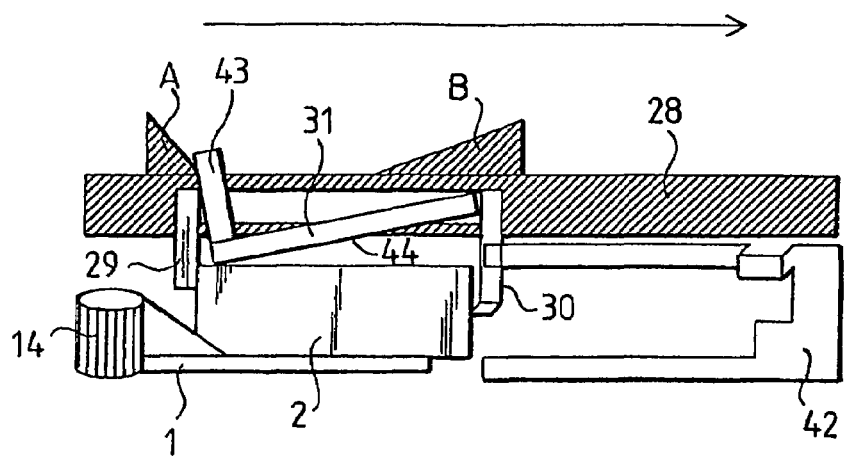
FIG. 9 is a side elevational view of the robot arm depicted as it retrieves a slide.
Figure 10:
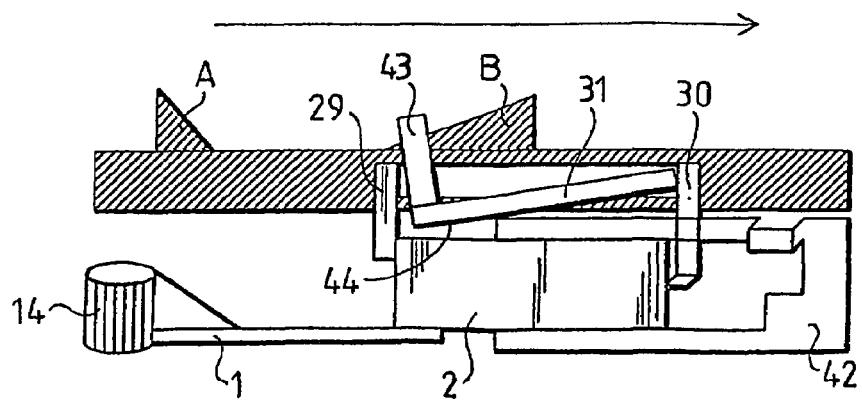
FIG. 10 is a side elevational view of the robot arm depicted as it advances a slide from the magazine into the slide holder of a microscope.

FIGS. 9 and 10 schematically show the operation of the robot arm 28 as it shifts a slide 2 from the magazine 1 into the slide holder 42 of a microscope. The rear and front arms 29 and 30 of the robot arm 28 and the hold-down plate 31 disposed between the arms 29, 30 are shown in both FIGS. 9 and 10. The upper corner of the hold-down plate 31 is designated at 43, while its lower edge is designated at 44. As the robot arm 28 extends, the motor 26 rotates the threaded control spindle 27 by the intermediary of the limit switch. As a result, the control spindle 27 moves the rear arm 29, the front arm 30 and the hold-down plate 31 toward the outer end of the slide feeding mechanism 18. By virtue of this arrangement the slide 2 situated between the rear and front arms 29, 30 and clamped by the hold-down plate 31 is introduced from the magazine 1 into the slide holder 42. The latter permits displacements of the slide 2 in front of the microscope objective during the course of image digitalization. The hypotenuses A and B of the right triangles show the path traveled by the upper corner 43 of the hold-down plate 31. As the hold-down plate 31 starts moving toward the end of the slide feeding mechanism 18, the dog 33 travels along the control track 35 which causes the upper corner 43 of the hold-down plate 31 to sink along the hypotenuse A, whereas its lower edge 44 pushes down the slide 2. As the control spindle 27 continues to rotate, the attached end of the hold-down plate 31 reaches the front dog 34 and then its lower edge 44 runs up on the dog 34, whereupon the upper corner 43 of the hold-down plate 31 rises along the hypotenuse B, releasing the slide 2 which thus enters the slide holder 42. Subsequently the rotation of the motor 26 is reversed, retracting the robot arm 28 and also, rotating the control spindle 27 in the opposite direction. As a result, the control spindle 27 drives backward the rear and front arms 29, 30, as well as the hold-down plate 31.

The construction according to the invention has many advantages with respect to the state of art: the construction and the use of the device is simple, and the invention is providing easy to handle and reliable components for a slide feeding unit.

A further advantage is that the magazines to be used and the others already used are always on different sides of the slide feeding device. In this way, the magazines can not be confused, moreover they can be fed or taken out during operation of the device.

The toothed rack on the magazine ensures improved localization of the slides. During the production of the magazines, namely, dimensional deviations of about 1% may be expected. This means that a deviation of 1 mm may occur at the last slide, when many slides are positioned to a given base surface and the feeding device will take a wrong slide as a consequence. In contrary to that, the dimensional deviations have no impact on the relation of the tooth of the rack to the slide guiding elements and, accordingly, the feeding device is always positioned to the right slide even in case of relatively great dimensional deviations.

Due to the above, the slides can be arranged very close to each other in the magazines without the risk of wrong feeding. The gap between the slides may be as small as 1 mm. In this way, a rather small magazine (120 mm×80 mm×30 mm) may contain 50 slides. This is about three times more then before.

It will be understood that the above description of the present invention is susceptible to various modifications, changes and adaptations, and the same are intended to be comprehended within the meaning and range of equivalents of the appended claims.

The invention claimed is:

1. A slide feeding unit for a microscope, comprising:
 a magazine for receiving slides; said magazine including:
  a base plate;
  two end walls;
  a side wall;
  an open side;
  a toothed rack secured externally to said side wall and being perpendicular to said base plate; and
  slide guiding elements oriented perpendicularly to said open side;
 a magazine moving mechanism including:
  a trough for receiving said magazine in a fitting relationship with said base plate and said end walls; said trough having opposite side plates, with one of said side plates being provided with openings;
  a first shaft disposed externally of one of the side plates, and extending therealong and parallel thereto;
  first drive means for rotating said first shaft;
  feeding gears rotatably supported in respective said openings of said side plate and being adapted to mesh with said toothed rack for advancing said magazine in a direction of advance;
  said first shaft including first driving worm gears adapted to mesh with said feeding gears;
  a pair of shafts rotatably supported by said trough and extending along said side plates respectively;
  second drive means for rotating said pair of shafts;

lifting gears rotatably held in said side plates and having inner faces substantially coplanar with an inner surface of said side plates; each lifting gear having two pins arranged at opposite ends of the lifting gear diameter and oriented perpendicularly to said inner face of the respective lifting gear; and second driving worm gears rotated by said pair of shafts and meshing with said lifting gears; and a slide feeding device traversing said trough and including:

a robot arm displaceable perpendicularly to said direction of advance of said magazine for removing a slide from said magazine; and third drive means for moving said robot arm.

2. The slide feeding unit according to claim 1, wherein the magazine moving mechanism is arranged in a backward tilted position, the base plate making an angle of about 10 to 45° with respect to a horizontal plane.

3. The slide feeding unit according to claim 1, wherein said slide guiding elements comprise rails disposed on said base plate of said magazine.

4. The slide feeding unit as defined in claim 1, wherein said third drive means comprises a motor and a control spindle rotated by said motor.

5. The slide feeding unit according to claim 4, wherein the third drive means further comprises a limit switch coupling said motor to said control spindle.

6. The slide feeding unit according to claim 5, wherein said motor has a motor shaft; and said limit switch includes:

a sleeve affixed to said motor shaft;

a helical spring wound externally on said sleeve and having a bent-out terminus; and a driven disk force-transmittingly coupled to said bent-out terminus and connected to said control spindle.

7. The slide feeding unit according to claim 1, wherein said robot arm comprises front and rear arms for moving the slides.

8. The slide feeding unit according to claim 1, wherein said slide feeding device comprises a hold-down plate for clamping the slides; said hold-down plate being secured to said robot arm for executing rocking motions with respect to said robot arm.

9. The slide feeding unit according to claim 8, further comprising dogs secured to said robot arm for controlling motions of said hold-down plate.

10. The slide feeding unit according to claim 1, wherein said magazine moving mechanism further comprises rails attached to said side plates of said trough for vertically guiding said magazine.

* * * * *